US009216956B2

(12) United States Patent
Svensson

(10) Patent No.: US 9,216,956 B2
(45) Date of Patent: Dec. 22, 2015

(54) DEUTERIUM-ENRICHED 4-HYDROXY-5-METHOXY-N,1-DIMETHYL-2-OXO-N-[(4-TRIFLUORO-METHYL)PHENYL]-1,2-DIHYDROQUINOLINE-3-CARBOXAMIDE

(75) Inventor: Leif Svensson, Rydeback (SE)

(73) Assignee: ACTIVE BIOTECH AB, Lund (SE)

( * ) Notice: Subject to any disclaimer, the term of this patent is extended or adjusted under 35 U.S.C. 154(b) by 0 days.

(21) Appl. No.: 14/125,666

(22) PCT Filed: Jun. 20, 2012

(86) PCT No.: PCT/EP2012/061798
§ 371 (c)(1),
(2), (4) Date: Dec. 12, 2013

(87) PCT Pub. No.: WO2012/175541
PCT Pub. Date: Dec. 27, 2012

(65) Prior Publication Data
US 2014/0112946 A1    Apr. 24, 2014

Related U.S. Application Data

(60) Provisional application No. 61/499,848, filed on Jun. 22, 2011.

(30) Foreign Application Priority Data

Jun. 22, 2011    (EP) .................................... 11171108

(51) Int. Cl.
C07D 215/00    (2006.01)
C07D 215/56    (2006.01)
A61K 31/4704    (2006.01)

(52) U.S. Cl.
CPC .......... *C07D 215/56* (2013.01); *A61K 31/4704* (2013.01)

(58) Field of Classification Search
None
See application file for complete search history.

(56) References Cited

U.S. PATENT DOCUMENTS 6,133,285 A * 10/2000 Bjork et al. ................... 514/312
2010/0055072 A1 * 3/2010 Gant et al. ................... 424/85.6

FOREIGN PATENT DOCUMENTS

| WO | 00/03991 | 1/2000 |
| WO | 01/30758 | 5/2001 |
| WO | WO 0130758 A1 * | 5/2001 |

OTHER PUBLICATIONS

Meanwell, N. J. Med. Chem. 2011 pp. 2529-2591.*
International Search Report dated Jul. 18, 2012, corresponding to PCT/EP2012/061798.

O. Bratt, et al.; "Open-Label, Clinical Phase I Studies of Tasquinimod in Patients with Castration-Resistant Prostate Cancer"; British Journal of Cancer; Oct. 20, 2009, vol. 101, No. 8; pp. 1233-1240.
Susan L. Dalrymple, et al.; " The Quinoline-3-Carboxamide Anti-Angiogenic Agent, Tasquinimod, Enhances the Anti-Prostate Cancer Efficacy of Androgen Ablation and Taxotere Without Effecting Serum PSA Directly in Human Xenografts"; Wilery Inter Science; Jan. 16, 2007; pp. 1-8.
Efficacy Working Party (EWP); Questions & Answers on the Use of Cocktail Studies for Investigating In Vivo Drug Interaction Potential; European Medicines Agency Pre-Authorisation Evaluation of Medicines for Human Use; Dec. 13, 2007; pp. 1-2.
Helene Gustavsson, et al.; "Transition of An Androgen-Dependent Human Prostate Cancer Cell Line Into an Androgen-Independent Subline Is Associated With Increased Angiogenesis"; Wiley-Liss, Inc.; 2005; pp. 364-373.
John T. Isaacs, et al.; "Identification of ABR-215050 as Lead Second Generation Quinoline-3-Carboxamide Anti-Angiogenic Agent fot the Treatment of Prostate Cancer"; Wiley-Liss, Inc.; 2006; pp. 1768-1778.
Karin Jennbacken, et al.; Prostate Cancer Progression Into Androgen Independency Is Associated With Alterations In Cell Adhesion and Invasivity; Wiley-Liss, Inc.; 2006; pp. 1631-1640.
Stig Jonsson, et al.; Synthesis and Biological Evaluation of New 1, 2-Dihydro-4-hydroxy-2-oxo-3-quinolinecarboxamides for Treatment of Autoimmune Disorders: Structure-Activity Relationship; J. Med. Chem; 2004; pp. 2075-2088.
Hans Postlind, et al.; "Response of Human CYP1-Luciferase Plasmids to 2,3,7,8-Tetrachlorodibenzo-p-dioxin and Polycyclic Aromatic Hydrocarbons"; Toxicology and Applied Pharmacology 118, Oct. 31,1992, pp. 255-262.
Research Report AARDA; List of Autoimmune and Autoimmune-Related Diseases; Oct. 24, 2013; pp. 1-6.
David E. Trentham; Arthritis and Rheumatism; Collagen Arthritis As a Relevant Model for Rheumatoid Arthritis; vol. 25, No. 8; Aug. 1982; pp. 911-916.
Clinical Phase-II study "EudraCT No. 2007-003470-26; Ref. 4 Trials-Summary"; Oct. 17, 2007.
Fisher Michael et al., "The complexities inherent in attempts to decrease drug clearance by blocking sites of CYP-mediated metabolism", Feb. 2006, pp. 101-109, Current opinion in drug discovery & development, vol. 9 No. 1, Ridgefield, CT 06877 USA.
Isaacs John et al., "Anti-cancer potency of tasquinimod is enhanced via albumin-binding facilitating increased uptake in the tumor microenvironment", Aug. 21, 2014, pp. 8093-8106, Oncotarget, vol. 5 No. 18.
Tung Roger et al., "The Development of Deuterium-Containing Drugs", Mar. 2010, entire article, Innovations in Pharmaceutical Technology issue 32, Concert Pharmaceuticals, Inc., Lexington, MA, USA 02421.
Tuvesson Helen et al., "In vitro metabolism and in vivo pharmacokinetics of quinoline 3-carboxamide derivatives in various species", Lund University, Sweden, Xenobiotica, Mar. 2005, vol. 35(3), pp. 293-304.

* cited by examiner

*Primary Examiner* — Heidi Reese
(74) *Attorney, Agent, or Firm* — Young & Thompson

(57) ABSTRACT

Deuterium-enriched 4-hydroxy-5-methoxy-N,1-dimethyl-2-oxo-N-[(4-trifluoromethyl) -phenyl]-1,2-dihydroquinoline-3-carboxamide, having a deuterium enrichment in the amide-N methyl group of at least 70%; or a salt thereof with a pharmaceutically acceptable organic or inorganic cation; and a method of preparing said compounds. The compounds are useful in therapy, e.g. for the treatment of a malignant hyperproliferative disorder or an autoimmune disease.

13 Claims, 7 Drawing Sheets

DEUTERIUM-ENRICHED 4-HYDROXY-5-METHOXY-N,1-DIMETHYL-2-OXO-N-[(4-TRIFLUORO-METHYL)PHENYL]-1,2-DIHYDROQUINOLINE-3-CARBOXAMIDE

FIELD OF THE INVENTION

The present invention relates to deuterium enriched 4-hydroxy-5-methoxy-N,1-dimethyl-2-oxo-N-[(4-trifluoro-methyl)phenyl]-1,2-dihydroquinoline-3-carboxamide, to pharmaceutically acceptable salts thereof, and to the use thereof in therapy.

BACKGROUND OF THE INVENTION

The compound 4-hydroxy-5-methoxy-N,1-dimethyl-2-oxo-N-[(4-trifluoromethyl)phenyl]-1,2-dihydroquinoline-3-carboxamide (CAS#254964-60-8, herein below also referred to as ABR-215050) has shown efficacy in animal experiments relevant for cancer (1). It also has been shown that ABR-215050 is capable of inhibiting prostate tumor growth via a mechanism involving an anti-angiogenic response (2); a clear anti-tumor response has been achieved in a number of in vivo tumor models using human prostate cancer cell lines (3). This has encouraged further trials on the compound and efficacy in the treatment of human cancer has been shown in a phase 2 clinical trial (4).

In a recent, randomized placebo-controlled double blind phase II clinical study of ABR-215050 in patients with asymptomatic metastatic castrate-resistant prostate cancer, a difference was shown in the number of patients with disease progression at six months. Indeed, the results showed that the fraction of patients with disease progression during the six month period was 31% for patients treated with ABR-215050, compared to 66% for placebo treated patients (p<0.0001). The median progression free survival was 7.6 months for the group treated with ABR-215050, compared to 3.2 months for the placebo group (p=0.0009). ABR-215050 treatment also had an effect on biomarkers relevant for prostate cancer progression and was generally well tolerated.

In vivo animal experiments further have shown that ABR-215050 also has an efficacy in the treatment of autoimmune diseases. Thus, an in vivo animal experimental study has shown efficacy of the compound in the treatment of rheumatoid arthritis (5), and another one has shown its efficacy in the treatment of multiple sclerosis (6).

Deuterium ($^2$H or D) is a stable and non-radioactive isotope of hydrogen which has approximately twice the mass of protium ($^1$H or H), the by far most common isotope of hydrogen. Deuteration of pharmaceuticals to improve pharmacokinetics (PK), pharmacodynamics (PD), and toxicity profiles has been disclosed previously with some classes of drugs. For example, it has been disclosed (7) that various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, (f) decrease the production of deleterious metabolites in specific tissues, and/or (g) create a more effective drug and/or a safer drug for polypharmacy, whether the polypharmacy be intentional or not. In (7), therefore, deuteration of laquinimod is disclosed and it is stated that the deuteration approach has the strong potential to slow the metabolism of laquinimod

SUMMARY OF THE INVENTION

According to a first aspect, there is provided a compound which is deuterium-enriched 4-hydroxy-5-methoxy-N,1-dimethyl-2-oxo-N-[(4-trifluoromethyl)phenyl]-1,2-dihydroquinoline-3-carboxamide, having a deuterium enrichment in the amide-N methyl group of at least 70%; or a pharmaceutically acceptable salt thereof.

There also is provided a method for preparing a deuterium-enriched 4-hydroxy-5-methoxy-N,1-dimethyl-2-oxo-N-[(4-trifluoromethyl)phenyl]-1,2-dihydro-quinoline-3-carboxamide having a deuterium enrichment in the amide-N methyl group of at least 70%; or a pharmaceutically acceptable salt thereof, by reacting a 4-hydroxy-5-methoxy-1-methyl-2-oxo-1,2-dihydro-quinoline-3-carboxylic acid C1-C4 alkyl ester with deuterated N-methyl-p-trifluoromethylaniline having a deuterium enrichment in the N-methyl group of at least 70%; in a suitable solvent; and optionally reacting the obtained compound with a suitable pharmaceutically acceptable base.

In one embodiment, the compound of the invention is according to formula (I)

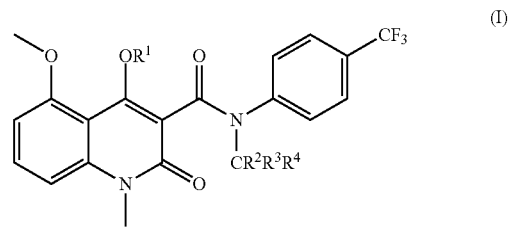

wherein $R^1$ is selected from H and pharmaceutically acceptable organic or inorganic cations;

$R^2$, $R^3$ and $R^4$ are independently selected from H and D; and $CR^2R^3R^4$ has a total deuterium enrichment of at least 70%.

There also is provided a method for preparing a compound according to formula (I)

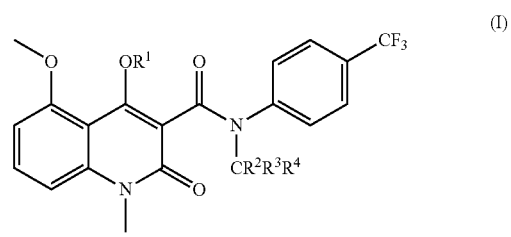

wherein $R^1$, $R^2$, $R^3$ and $R^4$ are as defined herein above;

comprising reacting a compound of formula (II)

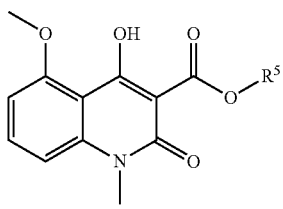

wherein $R^5$ is a C1-C4 alkyl group;
with a compound of formula (III)

in a suitable solvent; so as to obtain a compound of formula (I) wherein $R^1$ is H; and optionally reacting the compound of formula (I) wherein $R^1$ is H, with a suitable, pharmaceutically acceptable base.

The compound of the invention is useful as a medicament, e.g. for use in the treatment of a malignant hyperproliferative disease or an autoimmune disease.

The compound of the invention also is useful as a medicament, e.g. for use in the treatment of a disorder ameliorated by the modulation of immune function.

Consequently, there also is provided a pharmaceutical composition comprising a therapeutically effective amount of a compound according to the invention.

The inventive compound also is suitable for use in the prevention or treatment of a disorder selected from malignant hyperproliferative diseases and autoimmune diseases.

A method for the treatment of a mammal suffering from a malignant hyperproliferative disease also is provided. Furthermore, a method for the treatment of a mammal suffering from an autoimmune disease is provided, as well as a method for the treatment of a disorder that is ameliorated by the modulation of immune function.

DETAILED DESCRIPTION OF THE INVENTION

Figure 1:
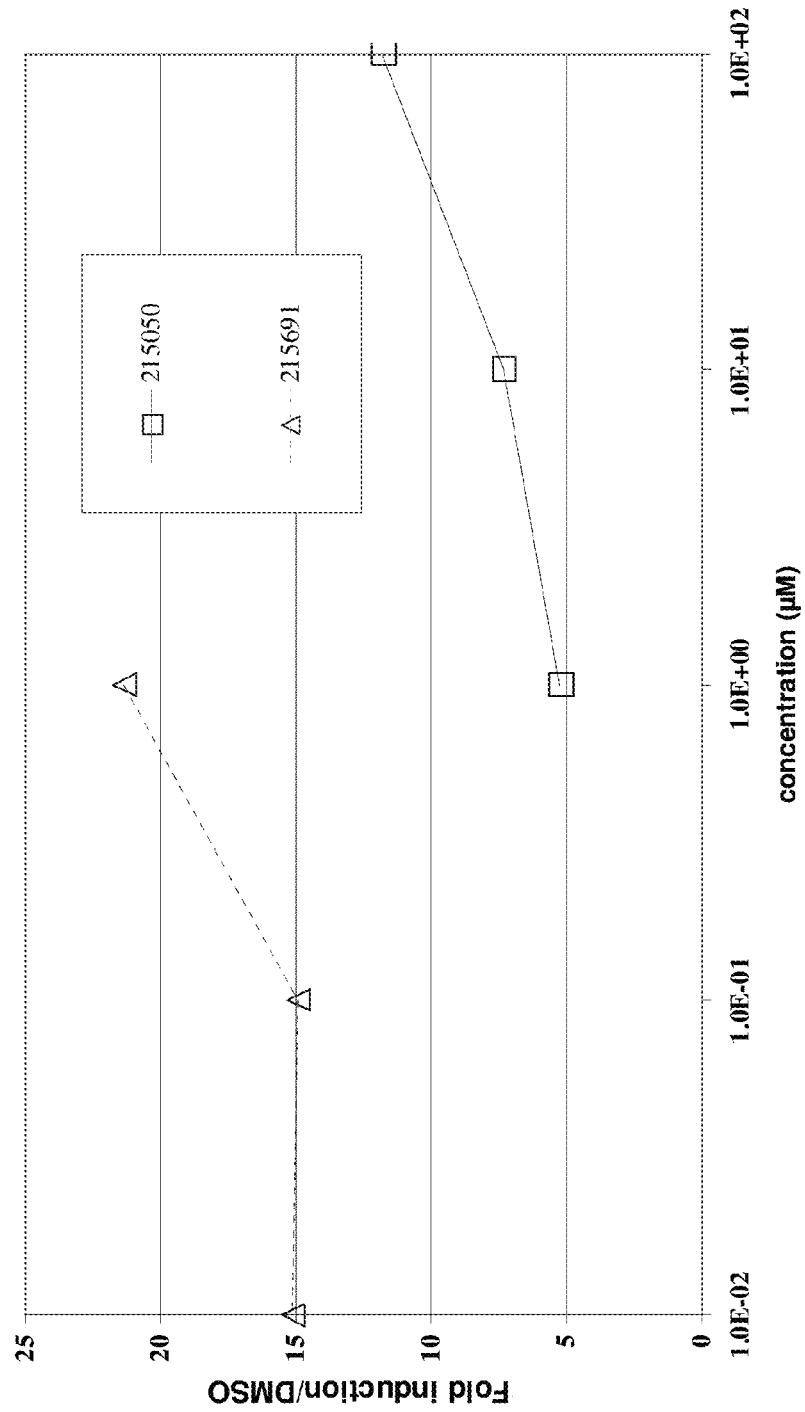
FIG. 1 is a graph representing the fold induction of luciferase expression as a function of added amounts of ABR-215050 and of its amide demethylation metabolite ABR-215691, respectively, in a human hepatoma cell line used in an in vitro luciferase gene reporter assay for the measurement of Ah mediated induction of CYP1A1.

As noted herein above, ABR-215050 has shown promising results as a therapeutically active compound which may be useful in the treatment of various serious diseases.

ABR-215050 was tested with respect to its CYP1A inducing capability in vitro in a TV-cell assay. This assay is a luciferase gene reporter assay developed for the measurement of AhR (Aryl hydrocarbon Receptor) mediated induction of CYP1A. Human CYP1A promoters and 5'-flanking sequences were cloned into firefly luciferase expression vectors and stably integrated into the human hepatoma cell line, HepG2 (9). The isolated cell line was renamed TV101L. This test showed that ABR-215050 did not induce CYP1A, cf. herein below under "In vitro assay of CYP1A inducing capacity of ABR-215050".

Three demethylation metabolites of ABR-215050 were found in the rat i.e. the quinoline-N demethylated metabolite, referred to herein below as ABR-219694, the quinoline-O demethylated metabolite ABR-222097, referred to herein below as ABR-222097, and the amide-N demethylated metabolite, referred to herein below as ABR-215691, cf. Table 1.

TABLE 1

Structural formula of ABR-215050 and its demethylation metabolites

| Compound identifier | Structural formula |
| --- | --- |
| ABR-215050 | |

TABLE 1-continued

Structural formula of ABR-215050 and its demethylation metabolites

| Compound identifier | Structural formula |
|---|---|
| ABR-219694 (quinoline-N demethyl) | (structure shown) |
| ABR-222097 (quinoline-O demethyl) | (structure shown) |
| ABR-215691 (amide-N demethyl) | (structure shown) |

These metabolites too were tested in the TV-cell assay. Just like ABR-215050, ABR-219694 and ABR-222097 were found not to induce CYP1A (data not shown). Surprisingly, it was found that in contrast to the parent compound and the two other demethylation metabolites, ABR-215691 had a substantial CYP1A inducing capacity, several magnitudes higher than that of the two other demethylated metabolites and the parent compound ABR-215050 itself, cf. herein below under "In vitro assay of CYP1A1 inducing capacity of ABR-215691". It could be suspected that even at a very low concentration, ABR-215691 could contribute substantially to CYP1A induction due to its very high inducing capacity.

The water solubility of ABR-215050 and of its metabolites also was investigated. It is a well-known fact that metabolism in general aims to transform compounds to more water soluble entities (10), which mostly decreases toxicity but also facilitates renal elimination. Both ABR-219694 and ABR-222097 were highly water soluble However, surprisingly ABR-215691 was found to have extremely low water solubility, compared to the other metabolites as well as to the parent compound, cf. Table 2.

TABLE 2

Water solubility of ABR-215050 and ABR-215691

| Compound | Water solubility at pH 7 (mg/mL) |
|---|---|
| ABR-215050 | 0.5 |
| ABR-215691 | <0.00001 |

In view of this low water solubility of ABR-215691 it may be expected that the renal excretion of ABR-215691 is low, compared to that of the two other demethylation metabolites. Together, the above findings indicate that CYP1A induction through ABR-215691 could eventually cause a drug to drug interaction problem in man in vivo that, even if not insurmountable, must nonetheless be seriously considered in medical treatment.

Therefore, the pharmacokinetic characteristics of the amide-N methyl deuterated ABR-215050 (herein below referred to as ABR-215050-dx), wherein the amide-N methyl moiety was tri-deuterated, compared to the non-deuterated parent compound were studied in rat. The reduction of the metabolic amide-N demethylation when the amide-N methyl was deuterium labeled was very pronounced; the formation of demethylated metabolite was diminished by as much as a factor of four compared to the non-deuterium labeled ABR-215050. In other words: relative to ABR-215050, the in vivo formation of ABR-215691 was reduced to only 25% when ABR-215050-dx was used. It also was noted that the reduced amide-N demethylation did not affect the 1:1 molar ratio for the parent drugs in vivo in plasma, meaning that the positive disease remedy effects are sustained but the undesired side effect consisting of CYP1A induction is depressed. cf. herein below under "In vivo investigation of pharmacokinetic characteristics of ABR-215050 and ABR-215050-dx in rat".

Further in vivo studies in rat show that CYP1A induction is substantially reduced by administration of ABR-215050-dx instead of ABR-215050 (cf. herein below under "In vivo investigation of CYP1A1/2 activity in rat after administration of ABR-215050 and ABR-215050-dx").

In vivo studies in mouse also show that ABR-215050-dx retains a high therapeutic activity (cf. herein below under "In vivo investigation of anti-tumor effect of ABR-215050-dx in mouse").

Thus, according to the present invention, a deuterated ABR-215050 is provided which on administration gives rise to a substantially reduced CYP1A induction while providing a high therapeutic activity.

For the purpose of the present invention, the term "deuterium enrichment" at a specific position of a compound refers to the percentage of incorporation of deuterium at that position in place of hydrogen. For example, by "a compound having a 90% deuterium enrichment at a given position" it is intended that 90% of the molecules in a sample contain deuterium at the specified position. The natural abundance of deuterium is about 0.0156%, which means that the natural deuterium enrichment at any specific position of a compound is 0.0156%. The deuterium enrichment can be determined using e.g. mass spectrometry and nuclear magnetic resonance spectroscopy.

When referring to a moiety, such as a methyl group, comprising several positions capable of being deuterated, the term "deuterium enrichment" refers to a mean value, based on the individual values for the positions in the moiety. As an illustrating example, for a moiety having a deuterium enrichment of 90% and comprising three specific deuteration positions, the deuteration enrichment at each individual position e.g. may be 85%, 92% and 93%, (or any other percentage values) the mean of which is 90%.

For the purpose of the present invention, disorders ameliorated by the modulation of immune function e.g. comprise malignant hyperproliferative diseases, such as cancer, autoimmune diseases, inflammation and inflammatory diseases, and hypersensitivity disorders of the immune system.

By "modulation of immune function" is meant e.g. mitigation or prevention of an immune response that causes undesirable effects.

As used herein, the terms "malignant hyperproliferative disease", "cancer" and "cancerous" refer to or describe a physiological condition in mammals that is typically characterized by unregulated cell growth. For the purpose of the present invention, examples of such a condition include, but are not limited to, melanoma, carcinoma, lymphoma, blastoma, sarcoma, and leukemia or lymphoid malignancies. More particular examples of such a condition include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "autoimmune disease" as used herein, refers to any disorder that occurs when the tissues of a living body are attacked by the body's own immune system. For the purpose of the present invention, examples of autoimmune diseases are: Acute Disseminated Encephalomyelitis (ADEM), Acute necrotizing hemorrhagic leukoencephalitis, Addison's disease, Agammaglobulinemia, Allergic asthma, Allergic rhinitis, Alopecia areata, Amyloidosis, Ankylosing spondylitis, Anti-GBM/Anti-TBM nephritis, Antiphospholipid syndrome (APS), Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Axonal & neuronal neuropathies, Balo disease, Behcet's disease, Bullous pemphigoid, Cardiomyopathy, Castleman disease, Celiac sprue, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic fasciitis, Erythema nodosum, Experimental allergic encephalomyelitis, Evans syndrome, Fibromyalgia, Fibrosing alveolitis, Giant cell arteritis (temporal arteritis), Glomerulonephritis, Goodpasture's syndrome, Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Insulin-dependent diabetes (type 1), Interstitial cystitis, Juvenile arthritis, Juvenile diabetes, Kawasaki syndrome, Lambert-Eaton syndrome, Leukocytoclastic vasculitis, Lichen planus, Lichen sclerosus, Ligneous conjunctivitis, Linear IgA disease (LAD), Systemic Lupus Erythematosus (SLE), chronic Lyme disease, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reflex sympathetic dystrophy, Reiter's syndrome, Relapsing polychondritis, Restless legs syndrome, Retroperitoneal Fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Ulcerative colitis, Undifferentiated connective tissue disease (UCTD), Uveitis, Vasculitis, Vesiculobullous dermatosis, Vitiligo, and Wegener's granulomatosis (11).

The term "hypersensitivity disorder" as used herein refers to a disorder such as allergy. Examples of allergy are atopic dermatitis, allergic urticarial, hay fever, allergic asthma, anaphylaxis, food allergy (milk, egg, peanut, tree nut, seafood, soy, wheat), penicillin allergy, etc The term "mammal" as used herein, includes a human as well as a non-human mammal, e.g. a horse, a pet animal, such as a cat or dog, a farm animal, such as a cow or sheep, or a laboratory animal such as a rat or monkey. Preferably the mammal is a human.

The term "treatment" as used herein includes prophylaxis as well as relieving the symptoms of disease. Thus, the term encompasses not only treating a patient to relieve the patient of the signs and symptoms of the disease or condition, or to ameliorate the condition of the patient suffering from the disease or disorder, but also prophylactically treating an asymptomatic patient to prevent the onset or progression of the disease or condition.

The term "effective amount" refers to an amount of a compound, which confers a therapeutic effect on the treated patient. The effect may be objective (i.e. measurable by some test or marker) or subjective (i.e. the subject gives an indication of or feels an effect).

As noted herein above, according to a first aspect, there is provided a compound which is deuterium enriched 4-hydroxy-5-methoxy-N,1-dimethyl-2-oxo-N-[(4-trifluoromethyl)phenyl]-1,2-dihydro-quinoline-3-carboxamide, having a deuterium enrichment in the amide-N methyl group of at least 70%, or a pharmaceutically acceptable salt thereof.

In some embodiments, the deuterium enrichment in the amide-N methyl group is at least 75%, or at least 80%, or at least 85%, e.g. at least 90%, or at least 95%, or at least 97%.

In some embodiments, the inventive compound is deuterated also at one or more other positions, i.e. it comprises a D instead of a H at a specific position which is not in the amide-N methyl moiety, at a deuterium enrichment in excess of 0.0156%.

There also is provided a method of preparing a compound as defined herein above, by reacting a 4-hydroxy-5-methoxy-1-methyl-2-oxo-1,2-dihydro-quinoline-3-carboxylic acid C1-C4 alkyl ester with deuterated N-methyl-p-trifluoromethylaniline having a deuterium enrichment in the amide N-methyl group of at least 70%; in a suitable solvent; and optionally reacting the compound with a suitable pharmaceutically acceptable base.

In some embodiments, the deuterium enrichment in the N methyl group of N-methyl-p-trifluoromethylaniline is at least 75%, or at least 80%, or at least 85%, e.g. at least 90%, or at least 95%, or at least 97%.

In some embodiments, either 4-hydroxy-5-methoxy-1-methyl-2-oxo-1,2-dihydro-quinoline-3-carboxylic acid C1-C4 alkyl ester or N-methyl-p-trifluoromethylaniline, or both, is deuterated at one or more further positions.

The "amide N" of 4-hydroxy-5-methoxy-N,1-dimethyl-2-oxo-N-[(4-trifluoromethyl)phenyl]-1,2-dihydro-quinoline-3-carboxamide also could be referred to as the "carboxamide N", i.e. it is the nitrogen of the 3-carboxamide moiety linking the phenyl ring moiety of the compound to the quinoline ring moiety. The "amide N-methyl", could also be referred to as the "carboxamide N-methyl" and is the methyl group attached to the (carbox)amide nitrogen.

The pharmaceutically acceptable salt of the compound of the invention may be e.g. a base addition salt derived from sodium hydroxide, potassium hydroxide, calcium hydroxide, monoethanolamine, diethanolamine, dimethylaminoethanol or morpholine.

In one embodiment, the inventive compound has the formula (I)

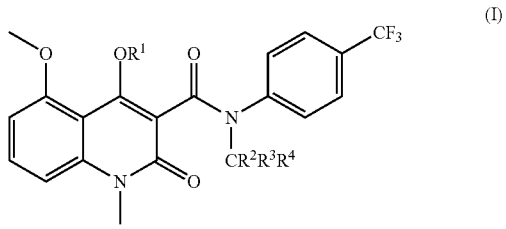

wherein

R$^1$ is selected from H and pharmaceutically acceptable organic or inorganic cations; and R$^2$, R$^3$ and R$^4$ are independently selected from H and D; and CR$^2$R$^3$R$^4$ has a total deuterium enrichment of at least 70%.

In some embodiments, R$^1$ is H. In other embodiments, R$^1$ is selected from pharmaceutically acceptable organic or inorganic cations, e.g. cations derived from sodium, potassium, calcium, monoethanolamine, diethanolamine, dimethylaminoethanol, and morpholine.

In formula (I), R$^2$, R$^3$ and R$^4$ are independently selected from H and D, each one of R$^2$, R$^3$ and R$^4$ having a deuterium enrichment such that CR$^2$R$^3$R$^4$ has a total deuterium enrichment of about at least 70%. In some embodiments, the deuterium enrichment of CR$^2$R$^3$R$^4$ is at least about 75%, or at least about 80%, or at least about 85%, e.g. at least about 90%, or at least about 95%, or at least about 97%.

For example, for a total deuterium enrichment of about at least 70%, the deuterium enrichment of each one of R$^2$, R$^3$ and R$^4$ should be at least about 89%; and for a deuterium enrichment of at least 97%, the deuterium enrichment of each one of R$^2$, R$^3$ and R$^4$ should be at least about 99%.

Preferably, R$^2$, R$^3$ and R$^4$ are all identical (R$^2$=R$^3$=R$^4$), i.e. the compound of the invention may be represented by formula (I'):

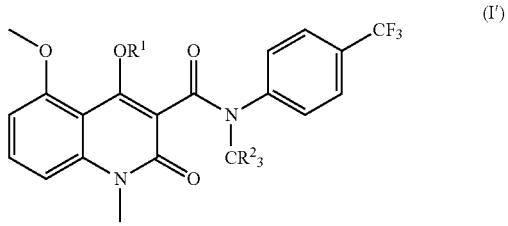

wherein R$^2$ is selected from H and D and CR$^2{}_3$ has a deuterium enrichment of at least 70%, or at least 75%, at least 80%, at least 85%, at least 90%, at least 95%, or at least 97%. In view of this, it should be realized that, unless otherwise indicated or apparent from the context, any reference made herein to a compound of formula (I) also should be understood to apply to a compound of formula (I').

It should be realised that any of the other hydrogen atoms of the compound according to formula (I) also may be exchanged for a deuterium. That is, in addition to R$^2$, R$^3$ and R$^4$, the compound of formula (I) may comprise up to 13 (when R$^1$ is not H) or 14 (when R$^1$ is H) further deuterium atoms replacing hydrogens in the compound of formula (I). Indeed, due to the natural distribution of deuterium a small fraction of the molecules in any given sample of the compound of formula (I) will comprise one or several deuterium atoms. However, the presence of such further deuterium atoms, either naturally or not, is not critical to the invention. Nonetheless, in some embodiments, the compound of formula (I) comprises at least one further deuterium atom at any specific location, other than in the amide-N methyl group, at a deuterium enrichment in excess of that which is naturally occurring, i.e. at an enrichment in excess of 0.0156%, for example a deuterium enrichment of at least 1%, or at least 5%, e.g. at least 10%. This further deuterium atom may replace a hydrogen atom at any location of the compound of formula (I). For example, one or more hydrogen atoms attached to any of the quinoline-N methyl group or the quinoline-O methyl group of the compound of formula (I) may be replaced by deuterium, and/or any of the aromatic hydrogens of the compound of formula (I) may be replaced by a deuterium.

There also is provided a method for preparing a compound according to formula (I) as defined herein above; by reacting a compound of formula (II)

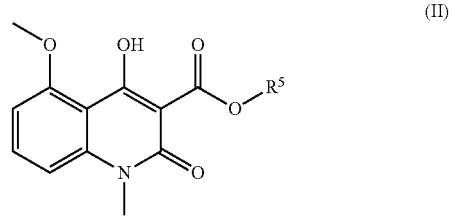

wherein R$^5$ is a C1-C4 alkyl group;
with a compound of formula (III)

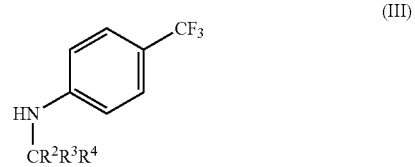

wherein R$^2$, R$^3$ and R$^4$ are as defined herein above, in a suitable solvent, and optionally reacting the compound of formula (I) wherein $R^1$ is H, with a suitable, pharmaceutically acceptable base, e.g. NaOH, KOH, Ca(OH)$_2$, monoethanolamine, diethanolamine, dimethylaminoethanol, or morpholine.

In the compound of formula (II), $R^5$ may be a C1-C4 alkyl group, e.g. a C1-C3 alkyl group, such as methyl or ethyl, in particular methyl.

The compound of formula (II) may comprise a deuterium at one or more locations at a deuterium enrichment in excess of that which is naturally occurring. Likewise, in the compound of formula (III) any of the aromatic hydrogens may be replaced by a deuterium atom at a deuterium enrichment in excess of that which is naturally occurring.

The reaction between the compounds of formula (II) and (III) is performed in a suitable solvent medium. The reaction solvent medium may be e.g. a hydrocarbon such as a straight or branched chain C7-C10 alkane or a cycloalkane or a mixture of thereof, e.g. heptane, octane or decahydronaphthalene.

The compound of the invention is useful in therapy. Thus, in some embodiments, the invention provides a compound for use in the treatment of a malignant hyperproliferative condition, e.g. selected from melanoma, carcinoma, lymphoma, blastoma, sarcoma, and leukemia or lymphoid malignancies. In some particular embodiments, the invention provides a compound for use in the treatment of a malignant hyperproliferative condition selected from squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, and head and neck cancer.

In some embodiments, the malignant hyperproliferative disease is selected from a solid tumor, malignant melanoma or a hematological tumor.

In some embodiments, the solid tumour is selected from adenocarcinoma, e.g. prostatic, breast, lung and colon-rectum cancers.

In some embodiments, the invention provides a compound for use in the treatment of an autoimmune disease, e.g an autoimmune disease as defined herein above.

In some particular embodiments, the autoimmune disease is selected from Crohn's disease, multiple sclerosis, rheumatoid arthritis, ulcerative colitis and systemic lupus erythematosus.

EXPERIMENTAL

In Vitro Assay of CYP1A1 Inducing Capacity of ABR-215050

The mechanism for transcription of CYP1A1 involves the binding of the inducer to the Ah receptor followed by a translocation of the ligand-Ah-receptor complex to the nucleus, where it binds to specific enhancer sequences in the 5'-flanking region of the CYP1A1 gene. These sequences are referred to as xenobiotic responsive elements (XREs).

A luciferase gene reporter assay was used for the measurement of AhR mediated induction of CYP1A1. Human CYP1A1 promoters and 5'-flanking sequences were cloned into firefly luciferase expression vectors and stably integrated into the human hepatoma cell line, HepG2 (8). The isolated cell line was renamed TV101L.

The cells were seeded in 96 well tissue culture plates 24-48 hours prior to treatment with the test compound. After the addition of ABR-215050 at a concentration of 1, 10 and 100 µM, the cells were further incubated for 12-24 hours. The cells were harvested by the addition of lysis buffer followed by a freezing/thawing cycle. An enzymatic assay was used for the determination of luciferase activity. The results, expressed as the fold induction of luciferase expression, are shown in Table 3 and in FIG. 1.

TABLE 3

| Luciferase gene reporter assay - ABR-215050 | |
|---|---|
| Conc. ABR-215050 µM | Fold induction of luciferase expression |
| 100 | 11.8 |
| 10 | 7.3 |
| 1 | 5.2 |

Figure 2:
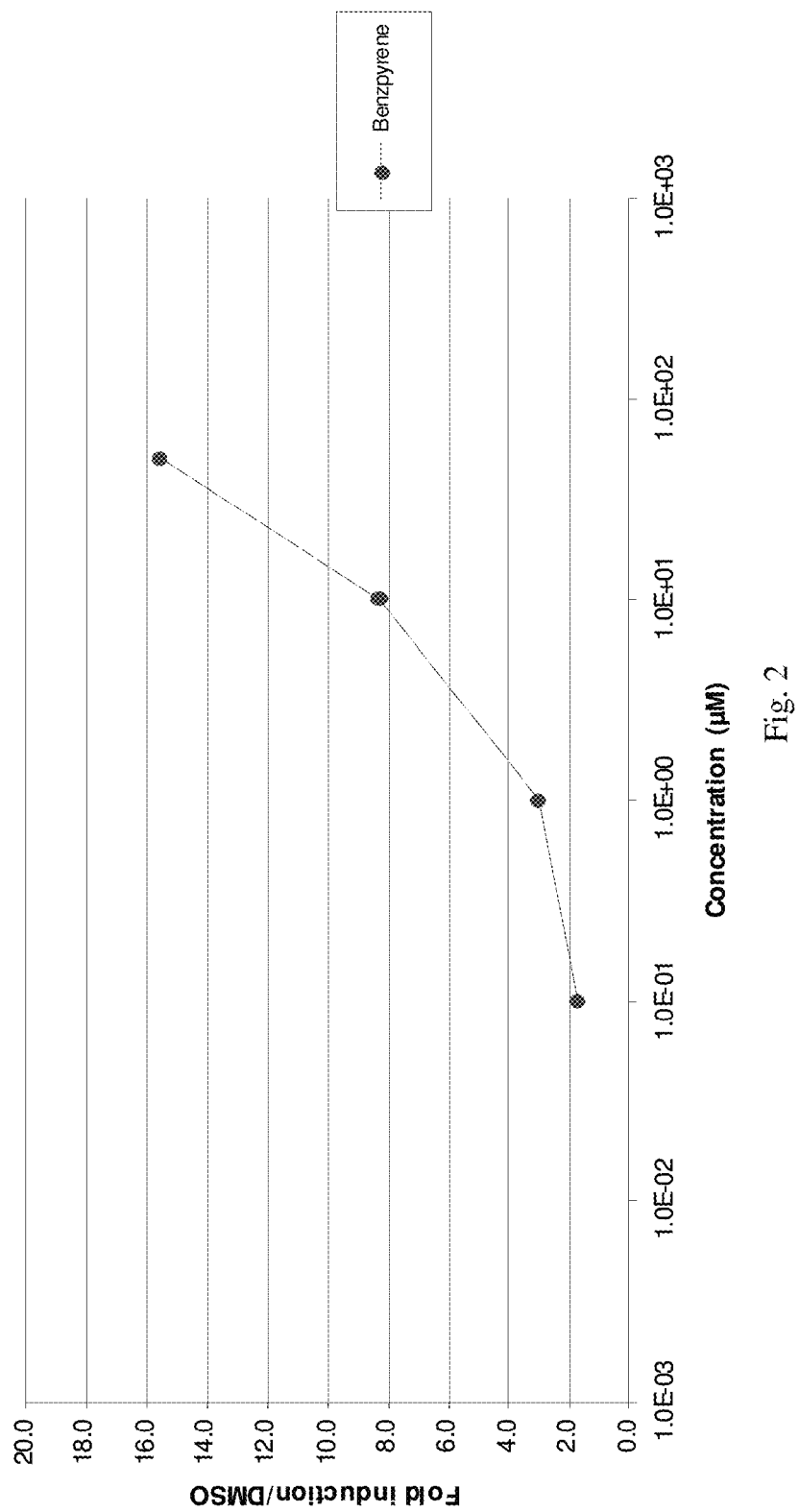
FIG. 2 is a graph representing the fold induction of luciferase expression as a function of added amounts of benzo(a)pyrene in a human hepatoma cell line used in an in vitro luciferase gene reporter assay for the measurement of Ah mediated induction of CYP1A1.

As a comparison, the same assay also was performed using benz(a)pyrene, a well-known, moderately strong CYP1A1 inducer. The results are shown in FIG. 2. The results of the in vitro assay show the extent of interaction of the tested compound with the Ah receptor, which mediates induction of both CYP1A1 and CYP1A2.

In Vitro Assay of CYP1A Inducing Capacity of ABR-215691

The same assay as used for ABR-215050 was used. The concentrations of ABR-215691 that were used and the results obtained, expressed as fold induction of luciferase expression, are shown in Table 4 and in FIG. 1.

TABLE 4

| Luciferase gene reporter assay - ABR-215691 | |
|---|---|
| Conc. of ABR-215691 µM | Fold induction of luciferase expression |
| 1 | 21.3 |
| 0.1 | 14.9 |
| 0.01 | 15.1 |

In Vivo Investigation of Pharmacokinetic Characteristics of ABR-215050 and ABR-215050-dx in Rat A deuterated (also referred to as deuterium-enriched) ABR-215050 was synthesized, wherein the amide-N methyl moiety was trideuterated (ABR-215050-dx). This deuterated compound was diluted with non-deuterated ABR-215050 to a molar ratio of 1:1. The 1:1 equivalent molar mixture was administrated to rats in an in vivo experiment. Because of additional 13-carbon labeling in the quinoline scaffold, the formed amide-N demethyl metabolites could be measured selectively by means of HPLC-MS (High performance Liquid Chromatography with Mass Spectrometric detection). In Table 5, the plasma levels of ABR-215050-dx and ABR-215050 (in nM) measured in 4 different rats are shown, as well as the ratio of these two compounds.

TABLE 5

Plasma levels of ABR-215050-dx and ABR-215050 in rat after a peroral dose of 2.5 mg/kg of each compound at time 0 h.

| Animal No | Time h | ABR-215050-dx nM | ABR-215050 nM | Ratio ABR-215050-dx/ABR-215050 |
|---|---|---|---|---|
| 1 | 1 | 13394 | 13807 | 0.97 |
| 2 | 2 | 13665 | 13859 | 0.99 |
| 3 | 3 | 7322 | 7382 | 0.99 |
| 4 | 4 | 17824 | 17814 | 1.00 |

From Table 5 it appears that the 1:1 ratio of the deuterated vs. non-deuterated parent compounds remain essentially unchanged in the animals for up to at least 4 hours at a peroral dosage of 2.5 mg/kg.

The plasma levels of the ABR-215691 derived from ABR-215050-dx and ABR-215050 also were determined using LC-MS/MS and the results are shown in Table 6, which also shows the calculated ratio of the plasma levels of ABR-215691 derived from ABR-215050-dx and from ABR-215050, respectively as well as the calculated reduction of formation of amide-N demethyl metabolite.

TABLE 6

Plasma levels of ABR-215691 from ABR-215050-dx and ABR-215050 in rat after a peroral dose of 2.5 mg/kg at time 0 h.

| Rat No | Time h | Plasma levels of ABR-215691 from ABR-215050-dx nM | Plasma levels ABR-215691 from ABR-215050 nM | Ratio of metabolite plasma levels | Reduction of amide-N demethylation % |
|---|---|---|---|---|---|
| 1 | 1 | 64.0 | 265 | 0.24 | 75.8 |
| 2 | 2 | 93.9 | 318 | 0.30 | 70.5 |
| 3 | 3 | 46.6 | 192 | 0.24 | 75.7 |
| 4 | 4 | 94.6 | 372 | 0.25 | 74.6 |
| | Mean | 74.8 | 286.8 | 0.26 | 74.1 |

Figure 5:
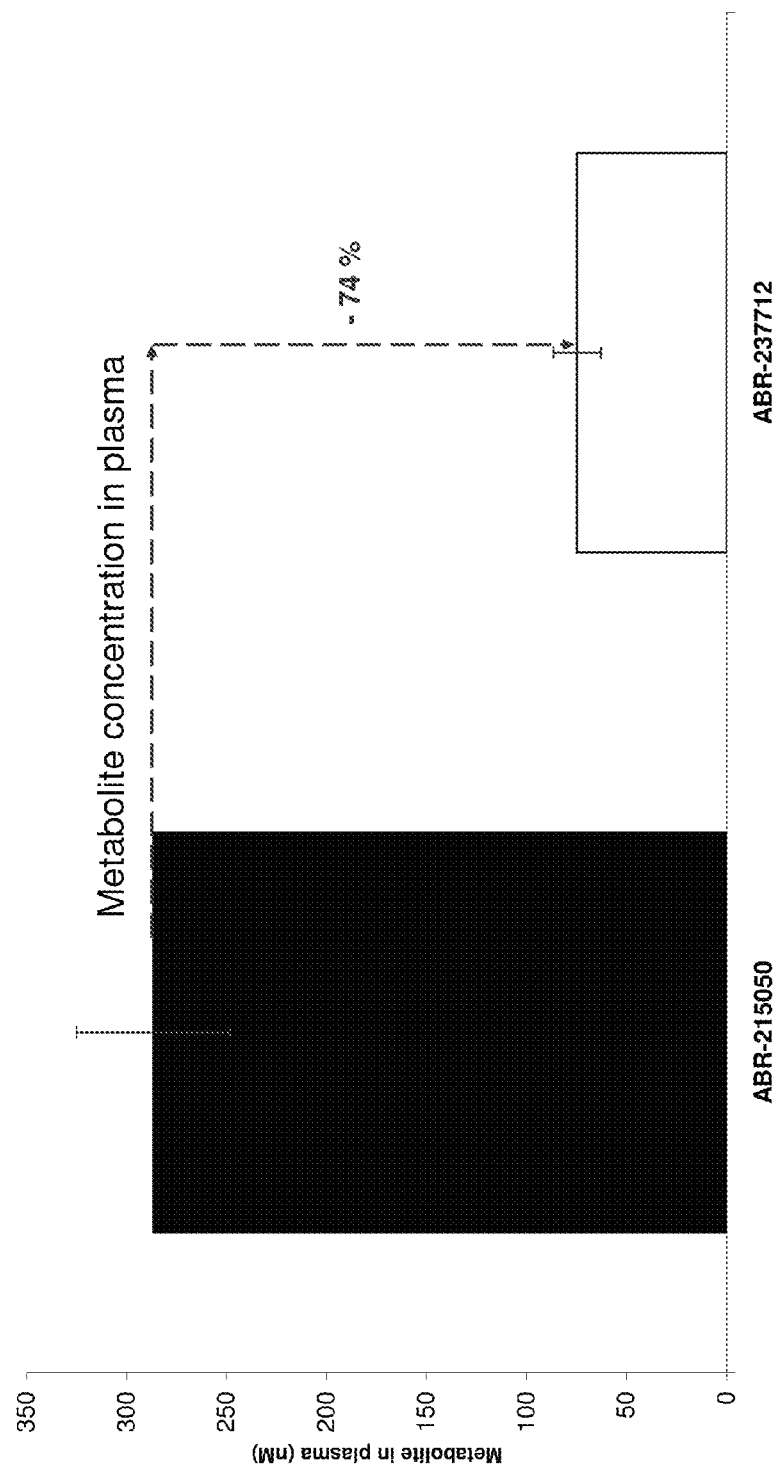
FIG. 5 is a bar diagram showing the mean plasma level (in nM) of the amide-N demethylated metabolite of ABR-215050 and of deuterium-enriched ABR-215050 wherein the amide-N methyl is deuterated, herein below also referred to as ABR-215050-dx, respectively, after administration to rat of ABR-215050 and ABR-215050-dx in a (1:1) mixture.

From Table 6 it appears that the formation of ABR-215691 is substantially reduced by deuteration of the amide-N methyl group. The reduction of amide-N demethylation obtained by said deuteration ranges from 70.5% to 75.8% over 4 hours following peroral dosage. The results are illustrated in FIG. 5.

In Vivo Investigation of CYP1A1/2 Activity in Rat After Administration of ABR-215050 and ABR-215050-dx The in vivo induction of CYP1A1 and CYP1A2 after repeated administration of ABR-215050 and of ABR-215050-dx, respectively, was studied in rat.

Test Preparations

Test preparations B and C and blank preparation A were made as follows: For preparation B, ABR-215050 was dissolved in NaOH and sterile water at a concentration of 0.5 mg/mL. The pH of the solution was adjusted to pH 7.4-8.5. Preparation C was made in the same way, using ABR-215050-dx. Preparation A was a blank containing only water. The preparations were stored in a refrigerator for a maximum of one week before use. Table 7 summarizes preparation data.

TABLE 7

| | Preparations | | |
|---|---|---|---|
| Preparation | Test compound | Conc. (ng/mL) | Volume (mL) |
| A | Water | — | 4 × 10 |
| B | ABR-215050 | 0.5 | 4 × 10 |
| C | ABR-215050-dx | 0.5 | 4 × 10 |

Test Animals

On arrival at the laboratory, the test animals were 9 weeks old Sprague Dawley male rats having a body weight of 250 g. They were divided into 3 groups and were allowed to acclimatize for at least 7 days before the test. During the whole acclimatization and test period, the animals received water and feed (Labfor R70, form Kimstad, Sweden) ad libitum, and were kept under a 12 hours dark/12 hours light cycle, at a temperature of 20±2° C. and a relative humidity of 50±15%.

Performance of Test

Before administration of any test preparation, the body weight of each animal was measured and the individual dose to be administered to an animal was determined based on the weight of the animal. Administration was performed perorally during 4 days, cf. Table 8.

TABLE 8

| | Administration data | | | | | |
|---|---|---|---|---|---|---|
| Group | Preparation | Conc. (mg/mL) | Dose (mg/kg) | Day of administration | Volume/ body weight (mL/kg) | Animal Nos. |
| 1 | A | 0 | 0 | 1-4 | 2 | 1-3 |
| 2 | B | 0.5 | 1 | 1-4 | 2 | 4-6 |
| 3 | C | 0.5 | 1 | 1-4 | 2 | 7-9 |

The animals were observed twice a day and weighed once a day. At any sign of reduced general condition, or at a weight loss of more than 15%, the rat was euthanized.

Sampling

Shortly before the final dose administration, a blood sample was taken from vena saphena of rat No. 5. At the end of the administration period (on day 4), blood samples were taken in heparinized tubes in order to analyze the plasma levels of the administered compounds and amide-N demethylated metabolite. The samples were withdrawn from vena saphena (approx. 250 μL of blood) and from vena cava (maximum volume possible) according to the schedule indicated in Table 9.

TABLE 9

Sampling schedule

| Rat No. | Time (after final dose) of sampling from vena saphena | Time (after final dose) of sampling from vena cava |
|---|---|---|
| 1 | — | 24 h |
| 2 | — | 24 h |
| 3 | — | 24 h |
| 4 | 2 h | 24 h |
| 5 | −4 h* | 24 h |
| 6 | 1 h and 7 h | 24 h |
| 7 | 2 h | 24 h |
| 8 | −4 h* | 24 h |
| 9 | 1 h and 7 h | 24 h |

*The sample is taken 4 hours before administration of final dose.

The samples were cooled in ice water and centrifuged at 1300×g, +4° C. for 10 minutes as soon as possible after withdrawal (within 30 minutes). Plasma was collected, frozen and kept at −70° C. until analysis.

Euthanization

At 24 h after administration of the final dose, the animals were weighed and from each animal a final blood sample was withdrawn for a pharmacokinetic analysis. The animals then were euthanized and from each one the liver was withdrawn, weighed, and immediately frozen in crushed dry ice. The livers then were stored at −70° C. until preparation of microsomes.

Preparation of Microsomes

Microsomes were prepared according to the method M-0287 "Preparation of subcellular fractions from animal tissues" and then kept at −70° C. until analysis.

Determination of Protein Concentration

The total protein concentration of the microsomal fraction was determined according to the method M-0289 "Determination of Protein according to Hartree".

Determination of CYP1A1/2 Enzyme Activity

The CYP1A1/2 enzyme activity was determined by incubation of the microsomal fraction with methoxyresorufin (MROD) and ethoxyresorufin (EROD), as CYP substrates, according to the method M-0272A, whereby EROD shows a higher specificity for CYP1A1, while MROD shows a higher specificity for CYP1A2.

The results are shown in Table 10.

Figure 6:
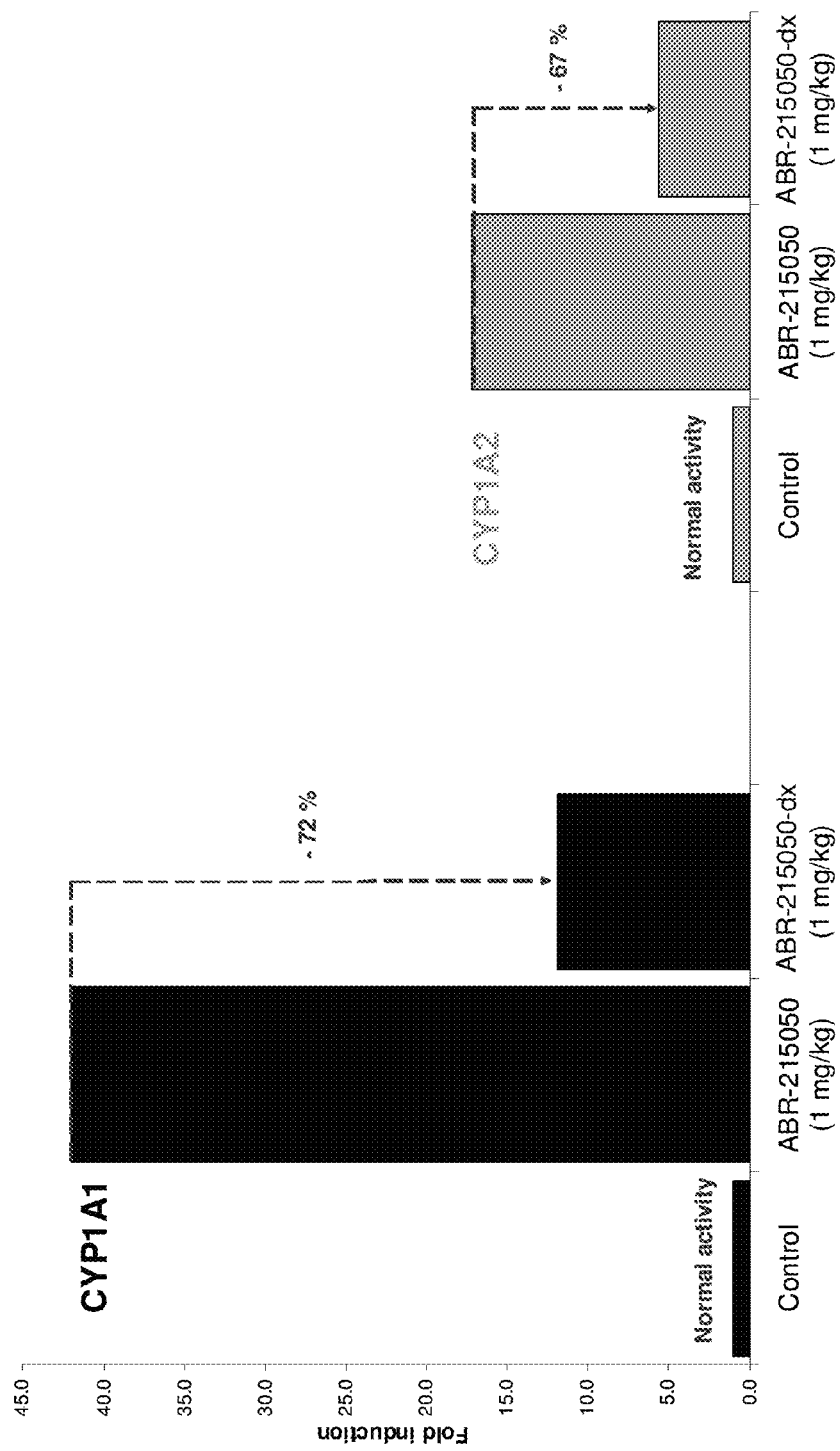
FIG. 6 is a bar diagram showing the mean fold induction of CYP1A1 and of CYP1A2 in rat after peroral administration of ABR-215050 and of ABR-215050-dx, with peroral administration of normal drinking water as blank.

According to the data represented in Table 10 the observed mean fold induction of CYP1A1 by ABR-215050 was 42, while ABR-215050-dx gave a mean fold induction of 11.5, which corresponds to a 73% reduction of the fold induction ((42-11.5)/42×100%) of CYP1A1. Table 11 also shows that ABR-215050 gave a mean fold induction of CYP1A2 of 17, while that obtained by administration of ABR-215050-dx was 5.5, i.e. a reduction of the fold induction of CYP1A2 of 68% ((17-5.5)/17×100%). The results are illustrated in FIG. 6.

In Vivo Investigation of Anti-Tumor Effect of ABR-215050-dx in Mouse

The anti-tumor effect of deuterated ABR-215050 was studied in mouse.

Cell Lines and Culture Conditions

The castration resistant subline LNCaP-19 was previously established from LNCaP cells (12). Cells were maintained as previously described (13). The LNCaP-19 cells were between passage 10 and 23 when used in the experiments. Passage 1 is defined as the first passage in our laboratory. The cells were tested and found free from mycoplasma.

Subcutaneous Implantation of Cells

Figure 7:
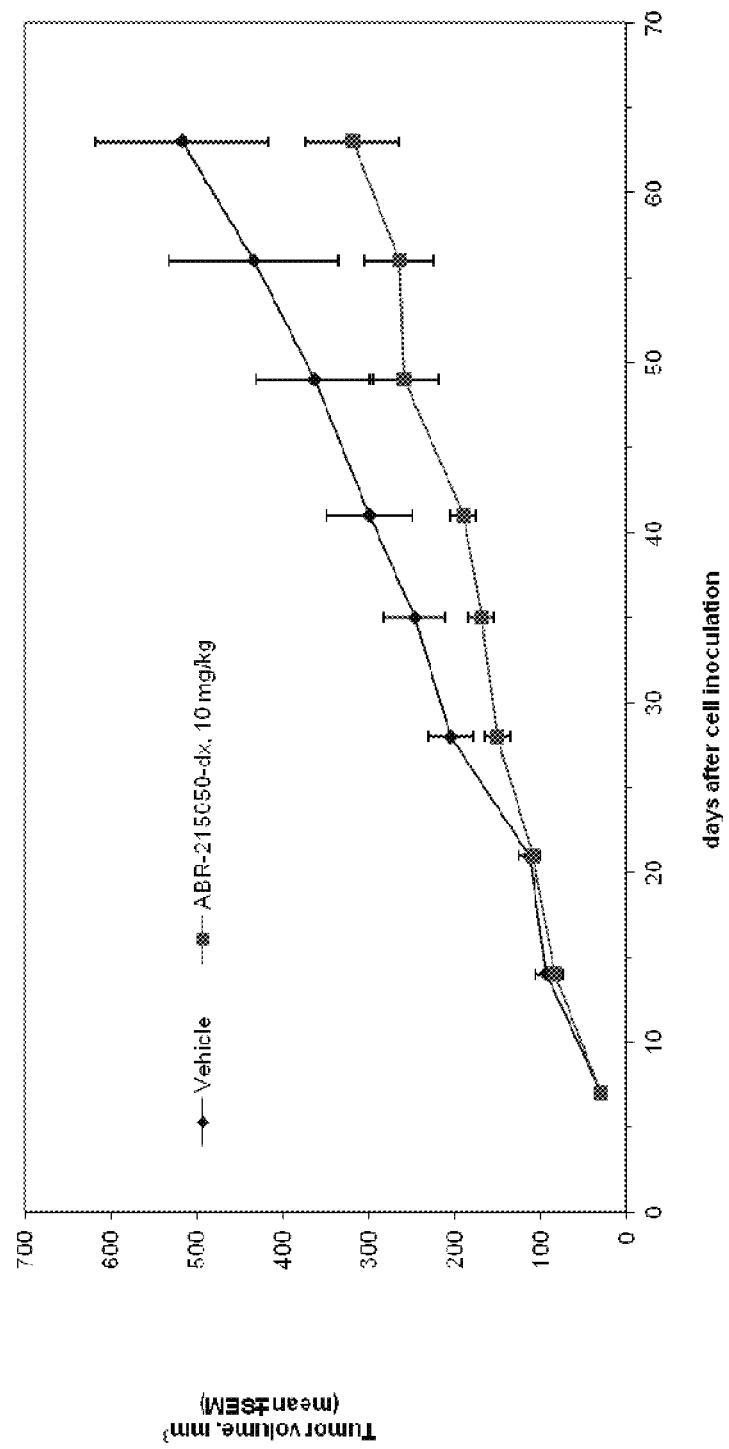
FIG. 7 is a diagram showing the effect of orally administered ABR-215050-dx (10 mg/kg/day) on LNCaP tumor in Nude Balb/c mice.

Male athymic Nude BALB/c mice (age 8 weeks) were purchased from Taconic (Lille Skensved, Denmark). For subcutaneous implantation, one million tumor cells suspended in 200 μl Matrigel (BD Bioscience, Bedford, Mass.) were inoculated on the flank of the mice. The tumor size was measured by a caliper once a week throughout the experiment and the tumor take was 75% in the untreated control group (n=12). In the tumor growth experiment, ABR-215050-dx (10 mg/kg/day) was administered via drinking water from day 7. To assure appropriate dose was given with no significant fluctuations, water consumption was monitored for each animal cage during the entire experiment. It has previously been shown that the plasma half-life of tasquinimod is 3.4 hours, and that administration of 1-10 mg/kg/day via drinking water results in steady state plasma levels (0.4-1 μM) (14). Animals were sacrificed when the average tumor size for the control group reached a volume of 900±100 mm$^3$ or when the tumor volume for an individual animal reached 1200 mm$^3$ The results are illustrated in FIG. 7.

The present invention is further illustrated in the following non-limiting Example.

EXAMPLE

4-Hydroxy-5-methoxy-N-deuteriomethyl-1-methyl-2-oxo-N-[(4-trifluoromethyl)phenyl]-1,2-dihydroquinoline-3-carboxamide 4-Hydroxy-5-methoxy-1-methyl-2-oxo-1,2-dihydroquinoline-3-carboxylic acid methyl ester (1.0 g, 3.79 mmol), N-deuteriomethyl-p-trifluoromethylaniline (1.0 g), tributylamine (100 microliter) and n-octane (70 mL) were heated to

TABLE 10

CYP1A1/2 induction in rat

Figure 3:
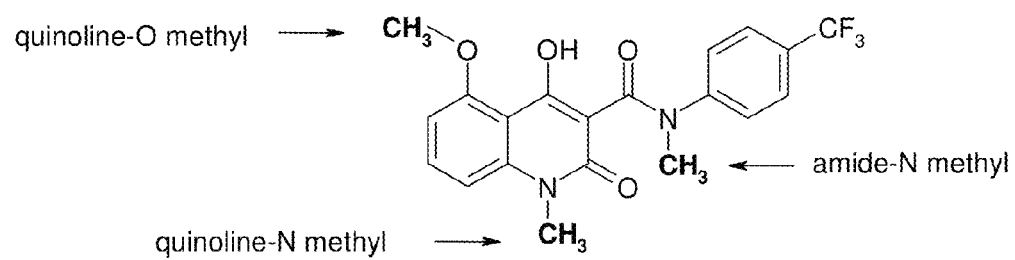
FIG. 3 is the structural formula of ABR-215050, showing in bold the three methyl groups that are present in the compound and that herein are referred to as amide-N-methyl, quinoline-N-methyl and quinoline-O-methyl, respectively.
Figure 4:
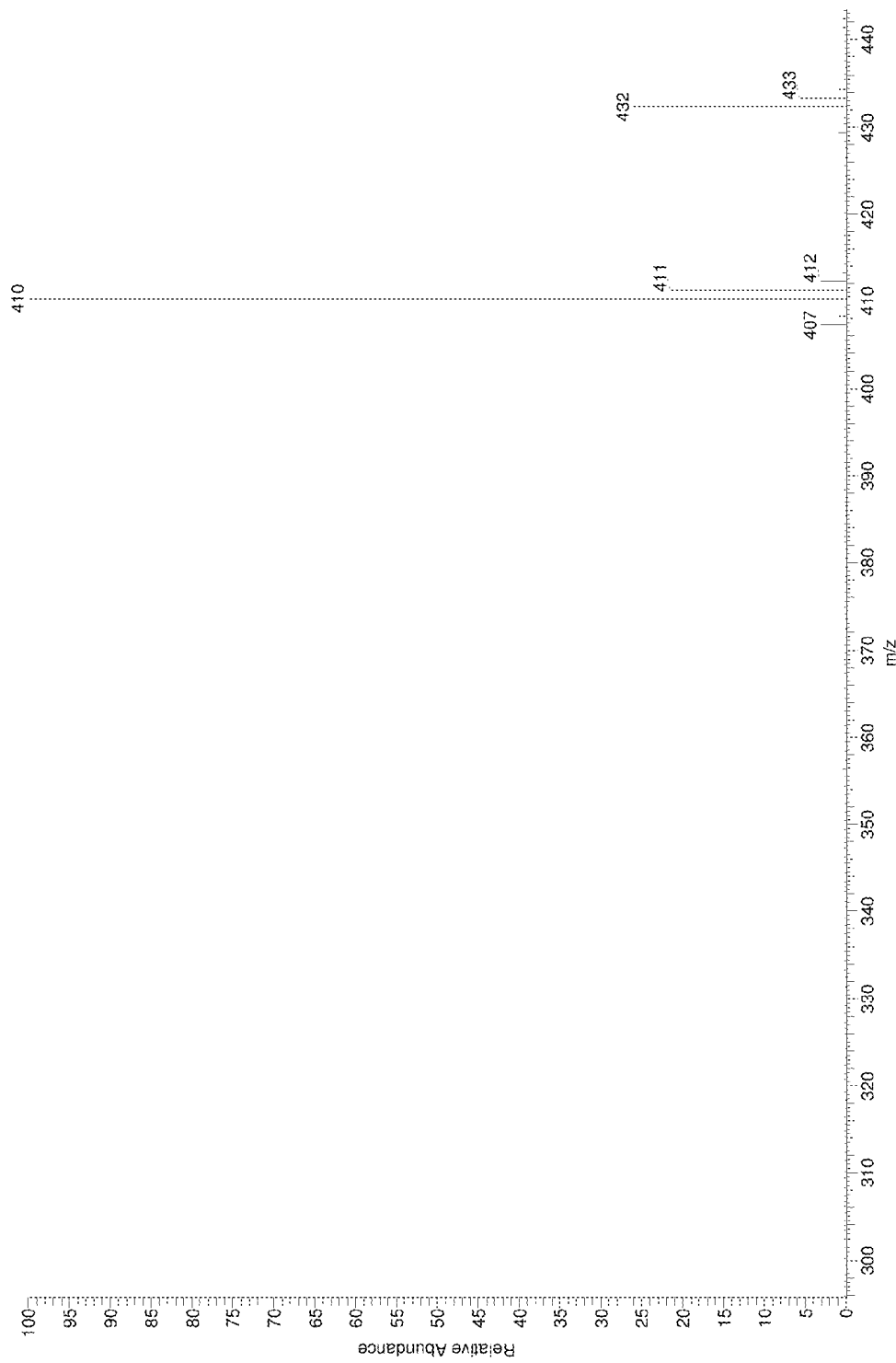
FIG. 4 is an electro spray ionization, positive mode, (ESI+) mass spectrum of ABR-215050 having a deuterated amide-N methyl group. Deuterium enrichment about 97%. Fraction of deuterium enriched compound represented in mass peak (protonated molecule, [M+H]+) at m/z=410 and fraction of not deuterium enriched compound represented in mass peak at m/z=407 (3% relative to m/z=410). The mass peak at m/z=432 is a molecular ion adduct formed due to sodium ionization [M+Na]+. The mass peaks at m/z=411, 412, 413 and 433 reflect the natural abundance of the isotopes $^{13}C$, $^{15}N$, $^{17}O$ and $^{18}O$.

| Group | Rat No | Treatment | CYP1A1 activity (EROD) (pmol/mg prot/min) | Mean | Fold induction | CYP1A2 activity (MROD) (pmol/mg prot/min) | Mean | Fold induction |
|---|---|---|---|---|---|---|---|---|
| 1 | 1 | water | 45 | 45 | | 17 | 20 | |
| | 2 | water | 45 | | | 22 | | |
| | 3 | water | | | | | | |
| 2 | 4 | ABR-215050 | 1342 | 1891 | 30 | 311 | 334 | 16 |
| | 5 | ABR-215050 | 2440 | | 54 | 357 | | 18 |
| | 6 | ABR-215050 | | | | | | |
| 3 | 7 | ABR-215050-dx | 556 | 534 | 12 | 95 | 111 | 5 |
| | 8 | ABR-215050-dx | 511 | | 11 | 126 | | 6 |
| | 9 | ABR-215050-dx | | | | | | | reflux and the volatiles were slowly distilled off during 6 hours. Approximately 60 mL solvents had distilled off at the end of the reaction and the mixture was cooled to room temperature. A mixture of n-heptane (25 mL) and toluene (6 mL) was added and the crystalline suspension was stirred for 20 min and the crystals were collected by filtration, washed with n-heptane, and dried to give the crude title compound (1.52 g). This was dissolved in a mixture of methanol (11.2 mL), water (6.8 mL) and sodium hydroxide (5 M, 0.83 mL, 4.15 mmol). Hydrochloric acid (5 M) was added to adjust the pH to approximately 8-9 and the mixture was filtered to remove any insoluble material. To the filtrate was added 5 M HCl until pH was approximately 2. The suspension was stirred for 1 hour and the crystals were collected by filtration, washed with 33% aqueous MeOH and then with water, and finally were dried in vacuum to give the title compound (1.25 g, 80%). H-nmr (CDCl$_3$); 9.95 (s, 1H), 7.50 (m, 5H), 6.93 (d, 1H), 6.70 (d, 1H), 4.04 (s, 3H), 3.55 (s, 3H). Anal. Calcd for $C_{20}H_{14}N_2D_3O_4F_3$: C, 58.68; H, 4.22; N, 6.84. Found: C, 58.8; H, 4.25; N, 6.94. Atmospheric pressure electrospray ionization (ESI) mass spectrometry: (M+H) calcd 410, found 410, cf. FIG. 3.

4-Hydroxy-5-methoxy-1-methyl-2-oxo-1,2-dihydroquinoline-3-carboxylic acid methyl ester was prepared by a method as described in (15).

The N-deuteriomethyl-p-trifluoromethylaniline was prepared as follows. 4-aminobenzotrifluoride (12.6 mL, 100 mmol) was dissolved in THF (100 mL) and trifluoroacetic anhydride (21.2 mL, 150 mmol) was added portionwise while cooling on an ice-bath. After complete addition the mixture was evaporated to give the trifluoroacetamide derivative as a white solid (26.1 g). This solid was dissolved in THF (100 mL) and cooled on an ice-bath. Potassium tert-butoxide (180 mmol, 20.2 g) and then deuteriomethyl iodide (25 g, 173 mmol) were added portionwise followed by stiffing at room temperature for 18 hours. The mixture was evaporated and partitionated between diethyl eter and water. The organic extract was washed with water and then brine and dried over sodium sulphate. Evaporation of the volatiles gave 2,2,2-trifluoro-N-deuteriomethyl-N-(4-trifluoromethyl-phenyl)-acetamide as a yellowish oil (27.3 g). This oil was dissolved in a mixture of methanol (125 mL) and ammonium hydroxide (28% aqueous solution, 50 mL). After stiffing at room temperature for 6 hours the mixture was concentrated and partitionated between diethyl eter and water. The organic extract was washed two times with water, then washed with brine and dried over sodium sulphate. Concentration gave a yellow oil that was purified on silica (heptane/ethyl acetate, 10:1-5:1) to give the title compound as a yellow oil (16.2 g, 91%). H-nmr (CDCl$_3$); 7.40 (d, 2H), 6.60 (d, 2H), 4.10 (s, 1H).

Thus, by providing deuterium-enriched ABR-215050 having a deuterated amide-N methyl group, the present inventor has provided a method to (a) reduce a specified unwanted metabolite with well-defined unwanted property, (b) without affecting the half-life of the parent drug, and (c) without formation of metabolites with unknown properties compared to the not deuterated compound.

Since the deuterated ABR-215050 according to the invention has a substantially reduced CYP1A inducing effect, the present invention in particular enables combination therapy with drugs that are susceptible of metabolization by CYP1A.

In case the compound of the invention is used in combination with another drug, the two components may be in the same formulation or in separate formulations for administration simultaneously or sequentially. The compounds of the present invention may also be used or administered in combination with other treatment such as irradiation for the treatment of cancer.

It also is contemplated that the reduction of the Cytochrome P450 CYP1A induction will allow for a possibility of increasing the dosage of ABR-215050 (in the amide-N methyl deuterated form), if this should be desired, even in the presence of drugs that are metabolised by CYP1A.

According to one aspect of the invention, there is provided a method for the treatment of a mammal suffering from of a disorder ameliorated by the modulation of immune function, which comprises administering to the mammal an effective amount of a compound according to the invention, or a pharmaceutically acceptable salt thereof.

In some embodiments, the treatment includes prophylaxis as well as relieving the symptoms of disease or disorder.

In some embodiments, the treatment is for relieving the symptoms of the disease, i.e. ameliorating the condition of the patient suffering from the disease or disorder.

Further, there is provided a method for the treatment of a malignant hyperproliferative disorder, e.g a malignant hyperproliferative disorder as mentioned herein above, or an autoimmune disease, e.g an autoimmune disease as mentioned herein above, in a mammal by administering to the mammal an effective amount of a compound according to the invention, or a pharmaceutically acceptable salt thereof.

Effective quantities of the compounds of formula (I) are preferably administered to a patient in need of such treatment according to usual routes of administration and formulated in usual pharmaceutical compositions comprising an effective amount of the active ingredient and a suitable pharmaceutically acceptable carrier. Such compositions may take a variety of forms, e.g. solutions, suspensions, emulsions, tablets, capsules, and powders prepared for oral administration, aerosols for inhalations, sterile solutions for parental administration, and suppositories for rectal administration or suitable topical formulations. Conventional procedures for the selection and preparation of suitable pharmaceutical formulations are described, for example, in "Aulton's Pharmaceutics: The Design and Manufacture of Medicines", M. E. Aulton, Churchill Livingstone, 2007.

A suitable daily dose for use in the treatment of cancer or an autoimmune disease is contemplated to vary between 0.0001 mg/kg to about 0.5 mg/kg body weight, in particular between 0.001 mg/kg to 0.05 mg/kg body weight, depending upon the specific condition to be treated, the age and weight of the specific patient, and the specific patient's response to the medication. The exact individual dosage, as well as the daily dosage, will be determined according to standard medical principles under the direction of a physician.

Various additives to enhance the stability or ease of administration of the drug are contemplated. The pharmaceutical composition may also contain additional therapeutically useful substances other than a compound of formula (I).

REFERENCES (1) PCT application WO 01/30758 A1.
(2) Isaacs J, Pili R, Qian D, Dalrymple S, Garrison J, Kyprianou N, Björk A, Olsson A, Leandersson T. Identification of ABR-215050 as lead second generation quinoline-3-carboxamide anti-angiogenic agent for the treatment of prostate cancer. Prostate. 2006 Dec. 1; 66(16):1768-78.
(3) Dalrymple S, Becker E, Isaacs J. The quinoline-3-carboxamide anti-angiogenic agent, tasquinimod, enhanced the anti-prostate cancer efficacy of androgen ablation and Taxotere without affecting serum PSA directly in human xenograft models. Prostate. 2007 67:790-797
(4) Clinical Phase-II study "EudraCT No: 2007-003470-26".
(5) Trentham D. E. 1982. Collagen arthritis as a relevant model for rheumatoid arthritis. Evidence pro and con. Arthr. Rheum. 25, 911-916
(6) International patent application No. WO00/03991
(7) US patent application No. 2010/0055072 A1
(8) London, 13 Dec. 2007 Doc. Ref. EMEA/CHMP/EWP/490784/2007 http://www.ema.europa.eu/docs/en_GB/document_library/Other/2009/11/WC500015483.pdf
(9) Postlind, H., Vu, T. P., Tukey, R. H., and Quattrochi, L. C. (1993). Response of Human CYP1-Luciferase Plasmids to 2,3,7,8-Tetrachlorodibenzo-p-dioxin and Polycyclic Aromatic Hydrocarbons. *Toxicol. Appl. Pharmco.* 118, 255-262
(10) Edward Kerns and Li Di. Drug-like Properties: Concepts, Structure Design and Methods: from ADME to Toxicity Optimization. Academic Press, 2008, ISBN 978-0-12-369520-8, p. 139
(11) The American Autoimmune Related Diseases Association, Inc. (AARDA) 22100 Gratiot Ave. East Detroit, Mich. 48021, USA http://www.aarda.org/research_display.php?ID=47
(12) Gustavsson H, Welen K, Damber J E. Transition of an androgen-dependent human prostate cancer cell line into an androgen-independent subline is associated with increased angiogenesis. Prostate. 2005; 62:364-73.
(13) Jennbacken K, Gustavsson H, Welen K, Vallbo C, Damber J E. Prostate cancer progression into androgen independency is associated with alterations in cell adhesion and invasivity. Prostate. 2006; 66:1631-40.
(14) Isaacs J T, Pili R, Qian D Z, Dalrymple S L, Garrison J B, Kyprianou N, Bjork A, Olsson A, Leanderson T. Identification of ABR-215050 as lead second generation quinoline-3-carboxamide anti-angiogenic agent for the treatment of prostate cancer. Prostate. 2006; 66:1768-78.
(15) Jönsson et al, J. Med. Chem., 2004, 47, 2075-2088.

The invention claimed is:

1. A method of preparing a deuterium-enriched 4-hydroxy-5-methoxy-N,1-dimethyl-2-oxo-N-[(4-trifluoromethyl)phenyl]-1,2-dihydroquinoline-3-carboxamide, or a pharmaceutically acceptable salt thereof, comprising reacting a C1-C4 alkyl ester of 4-hydroxy-5-methoxy-1-methyl-2-oxo-1,2-dihydro-quinoline-3-carboxylic acid with deuterium-enriched N-methyl-p-trifluoromethylaniline, wherein the N-methyl group has a deuterium enrichment of at least 70%.

2. The method according to claim 1, wherein a compound of formula (II)

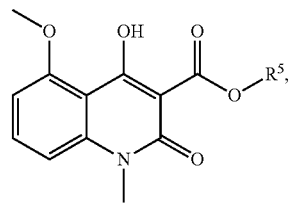

wherein $R^5$ is a C1-C4 alkyl group,
is reacted with a compound of formula (III)

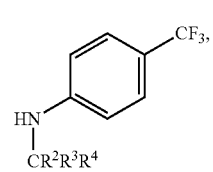

wherein $R^2$, $R^3$ and $R^4$ are independently selected from H and D; and $CR^2R^3R^4$ has a total deuterium enrichment of at least 70%,
so as to obtain a compound of formula (I)

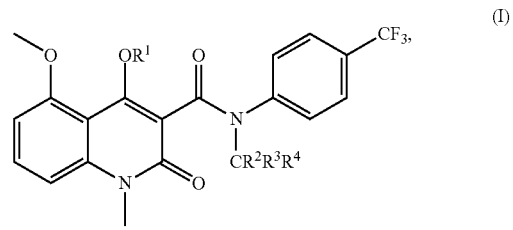

wherein $R^1$ is H.

3. The method according to claim 1, wherein the deuterium enrichment is at least 90%.

4. The method according to claim 1, further comprising reacting the deuterium-enriched 4-hydroxy-5-methoxy-N,1-dimethy-2-oxo-N-[(4-trifluoromethyl)phenyl]-1,2-dihydroquinoline-3-carboxamide with a pharmaceutically acceptable organic or inorganic base, to produce said pharmaceutically acceptable salt thereof.

5. The method according to claim 4, wherein the base is selected from the group consisting of sodium hydroxide, potassium hydroxide, calcium hydroxide, monoethanolamine, diethanolamine, dimethylaminoethanol and morpholine.

6. The method according to claim 1, wherein said C1-C4 alkyl ester of 4-hydroxy-5-methoxy-1-methyl-2-oxo-1,2-dihydro-quinoline-3-carboxylic acid is a C1-C3 alkyl ester.

7. The method according to claim 6, wherein the C1-C4 alkyl ester is methyl or ethyl ester.

8. The method according to claim 6, wherein the C1-C4 alkyl ester is methyl ester.

9. The method according to claim 2, further comprising reacting the compound of formula (I) with a pharmaceutically acceptable organic or inorganic base, to produce said pharmaceutically acceptable salt thereof.

10. The method according to claim 9, wherein the base is selected from the group consisting of sodium hydroxide, potassium hydroxide, calcium hydroxide, monoethanolamine, diethanolamine, dimethylaminoethanol and morpholine.

11. The method according to claim 2, wherein $R^5$ is a C1-C3 alkyl ester.

12. The method according to claim 2, wherein $R^5$ is methyl or ethyl ester.

13. The method according to claim 2, wherein $R^5$ is methyl ester.

\* \* \* \* \*